(12) United States Patent
Ducros et al.

(10) Patent No.: US 11,226,325 B2
(45) Date of Patent: Jan. 18, 2022

(54) METHOD FOR SIMULATING THE QUANTITY AND THE QUALITY OF THE HYDROCARBONS FROM A SEDIMENTARY BASIN

(71) Applicant: IFP Energies nouvelles, Rueil-Malmaison (FR)

(72) Inventors: Mathieu Ducros, Rueil-Malmaison (FR); Renaud Traby, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 490 days.

(21) Appl. No.: 16/375,162

(22) Filed: Apr. 4, 2019

(65) Prior Publication Data

US 2019/0369078 A1    Dec. 5, 2019

(30) Foreign Application Priority Data

Apr. 5, 2018    (FR) .................................... 18/52.943

(51) Int. Cl.
*G01N 33/24*    (2006.01)
*G01V 11/00*    (2006.01)
(Continued)

(52) U.S. Cl.
CPC .........  *G01N 33/241* (2013.01); *G01V 11/002* (2013.01); *E21B 43/16* (2013.01); *E21B 49/003* (2013.01); *G01V 11/00* (2013.01)

(58) Field of Classification Search
CPC ............. G01V 2210/62; G01V 99/005; G01V 11/002; E21B 49/003; E21B 43/16; G01N 33/241
See application file for complete search history.

(56) References Cited

U.S. PATENT DOCUMENTS 5,843,787 A    12/1998    Trabelsi et al.
2010/0228485 A1    9/2010    Betancourt et al.
(Continued)

FOREIGN PATENT DOCUMENTS

CN    106837317 A    6/2017
EP    0691540 A1    1/1996
(Continued)

OTHER PUBLICATIONS

Chen, Quick Evaluation of Source Rock Kerogen Kinetics Using Hydrocarbon Pyrograms from Regular Rock-Eval Analysis, Energy & Fuels 2017 31 (2), 1832-1841, DOI: 10.1021/acs.energyfuels. 6b01569 (Year: 2017).*

(Continued)

*Primary Examiner* — Michael J Dalbo
(74) *Attorney, Agent, or Firm* — Fitch, Even, Tabin & Flannery LLP

(57) ABSTRACT

The invention is a method for determining at least one of the quantity and the quality of the hydrocarbons generated by maturing of the organic material of a mother rock of a sedimentary basin based on values representing the artificial maturation of an immature sample representing the mother rock and a sequence of artificial maturing temperatures. The method according to the invention determines the values of the kinetic parameters of a reaction rate law by minimizing simultaneously: (i) a difference between the values predicted by the reaction rate law applied with a historical record of temperatures of the basin determined by basin simulation and the measurements of the advance of the maturation of the organic material and (ii) a difference between the values predicted by the reaction rate law applied according to the sequence of temperatures for the artificial maturing and the values representing the artificial maturing.

15 Claims, 2 Drawing Sheets

(51) Int. Cl.
*E21B 43/16* (2006.01)
*E21B 49/00* (2006.01)

(56) References Cited

U.S. PATENT DOCUMENTS

2014/0377872 A1* 12/2014 Brosse .................. G01V 11/00
                                                                  436/29
2015/0346179 A1* 12/2015 Pillot .................. G01N 33/241
                                                                  702/2
2017/0167230 A1*  6/2017 Ducros .................. G06F 30/20

FOREIGN PATENT DOCUMENTS

| EP | 2816377 A1 | 12/2014 |
| WO | 2014/040622 A1 | 3/2014 |

OTHER PUBLICATIONS

Preliminary Search Report dated Nov. 29, 2018 (2 pages).

* cited by examiner

METHOD FOR SIMULATING THE QUANTITY AND THE QUALITY OF THE HYDROCARBONS FROM A SEDIMENTARY BASIN

CROSS REFERENCE TO RELATED APPLICATIONS

Reference is made to French Application No. 18/52.943 filed Apr. 5, 2018, which is incorporated herein by reference in its entirety.

BACKGROUND OF THE INVENTION

Field of the Invention

The present invention relates to exploration and exploitation of petroleum deposits or geological gas storage sites.

Description of the Prior Art

Petroleum exploration searches for hydrocarbon deposits in a sedimentary basin. Understanding the principles of the genesis of the hydrocarbons and their links with the geological history of the subsoil has enabled the development of methods for evaluation of the petroleum potential of a sedimentary basin. The general approach to the evaluation of the petroleum potential of a sedimentary basin involves to-and-fro transitions between:

a prediction of the petroleum potential of the sedimentary basin based on available information concerning the basin under study (outcrops, seismic campaigns, drilling, for example); this prediction is aimed at:
  a better understanding of the architecture and the geological history of the basin under study, notably whether hydrocarbon maturing and migration processes have been able to take place;
  identifying zones of the subsoil in which those hydrocarbons have been able to accumulate;
  defining which zones have the best economic potential as evaluated on the basis of the volume and the nature of the hydrocarbons probably trapped (viscosity, level of mixing with water, chemical composition, etc.), and the cost of exploitation thereof (controlled for example by depth and the fluid pressure); and
exploratory drilling in the various zones having the best potential in order to confirm or to rule out the previously predicted potential and to acquire new data to be fed into new and more precise studies.

The exploitation of a petroleum deposit selects on the basis of information collected during the petroleum exploration phase the zones of the deposit having the best petroleum potential, defining optimum exploitation schemes for those zones (for example by use of a reservoir simulation in order to define the number and positions of exploitation wells enabling optimum hydrocarbon recovery), drilling exploitation wells and, as a general rule, installing the production infrastructures necessary for the development of the deposit.

In some sedimentary basins that have a complicated geological history involving numerous physical processes or when the volume of data is very large, the evaluation of the petroleum potential of a sedimentary basin requires computer tools enabling synthesis of the available data and computer tools enabling simulation of the geological history and the multiple physical processes that control it. This is a so-called "basin modelling" approach. The family of so-called basin modelling software enables the simulation in one, two or three dimensions of the sedimentary, tectonic, thermal, hydrodynamic and organic and inorganic chemical processes involved in the formation of a petroleum basin.

Basin modelling classically includes three steps:

A step of construction of a meshed representation of the basin under study, known as geo-modelling. This meshed representation is most often structured in layers, that is a group of meshes is assigned to each geological layer of the modelled basin. Then, each mesh of that meshed representation is filled with one or more petrophysical properties such as porosity, facies (clay, sand, etc.) or again their organic material content at the moment of their sedimentation. The construction of this model is based on data acquired during seismic campaigns, measurements in wells, core samples, etc.

A step of structural reconstruction of this meshed representation representing earlier states of the architecture of the basin. This step may be carried out by use of a so-called "backstripping" method (Steckler et al., 1978) or by a so-called structural restoration method (EP 2110686).

A step of numerical simulation of a selection of physical phenomena occurring during the evolution of the basin and contributing to the formation of the petroleum traps. This step, known as "basin simulation", relies on a discretized representation of space and time. In particular, a basin simulation provides a predictive map of the subsoil, indicating the probable location of the deposits, and the concentration, the nature and the pressure of the hydrocarbons trapped therein.

By providing quantitative and reliable information, this integrated basin modelling approach makes it possible to increase the success rate on drilling an exploratory well.

Basin simulation tools are known that enable numerical simulation of the formation of a sedimentary basin. There may be cited for example the tool described in the EP patent 2110686 corresponding to U.S. Pat. No. 8,150,669 or EP patent applications 2816377 corresponding to US published application 2014/0377872, FR 3075947 corresponding to US published application 2016/0290107, and FR 3182176 corresponding to US published application 2017/0177764. These tools notably enable estimation of the evolution of the temperature in the whole of a sedimentary basin over geological time periods.

Known petroleum reserves correspond essentially to fluids of organic origin. Organic material is highly variable in terms of elementary composition and hydrocarbon generation potential. These variations are explained on the one hand by the very origin of the organic material, which may come from marine microorganisms, lacustrine algae or higher plants, for example, and on the other hand the state of preservation of that organic material, which can in particular be oxidized or degraded by microorganisms.

The principal steps of the evolution of the organic material are very strongly linked to the increase in the temperature in the subsoil caused in particular by the progressive burial of the sediments (Vandenbroucke and Largeau, 2007). The step of catagenesis includes the transformation of kerogen into hydrocarbons. This transformation of the organic material is a function of time and temperature (Ungerer 1990; McNab et al., 1952; Pitt, 1961; Philippi, 1965; Louis et Tissot, 1967).

It is important for reliable prediction of the quantities of hydrocarbons produced by the mother rocks in sedimentary basins that these basin models simulate as realistically as possible the transformation of the organic material in a basin over geological time periods. Such simulation may be based on a quantitative model of transformation of the organic material present in the mother rock of the basin under study combined with prediction of the evolution of the temperature in the basin.

The following documents are cited in the course of the description:

John G. Stainforth, Practical Kinetic Modeling of Petroleum Generation and Expulsion. Marine and Petroleum Geology Volume 26, Issue 4, April 2009, Pages 552-572

Pepper and Corvi, 1995, Simple Kinetic Models of Petroleum Formation Marine and Petroleum Geology 12(3): 291-319

Ungerer, 1990, State of the Art of Research in Kinetic Modelling of Oil Formation and Expulsion Org. Geochem. Vol. 16, Nos 1-3, pp. 1-25, 1990

McNab, J. G., Smith, P. V., Jr and Betts, R L., 1952, The Evolution of Petroleum. Ind. Engin. Chem., 44, 2556

Pitt, G. J., 1961, The Kinetics of the Evolution of Volatile Products from Coal. In: 4th International Conference on Coal Science, Le Touquet, France, 30 May-2 Jun. 1961.-2563.

Louis, M. C. and Tissot, B. P., 1967, Influence de la Température et de la Pression sur la Formation des Hydrocarbures dans les argiles à Kérogène. In: Proceedings, 7th World Petroleum Congress, Mexico, Vol. 2, 47-60.

Philippi, G. T., 1965, On the Depth, Time and Mechanism of Petroleum Generation. Geochim. Cosmochim. Acta, 29, 1021-1049.

Jean Burrus, 1997, Contribution à l'Étude du Fonctionnement des Systemes Pétrohers: Apport d'une Modelisation Bi-dimensionnelle, Doctoral Thesis Behar, F., Leblond, C. and Saint-Paul, C., 1989, Analyse Quantitative des Effluents de Pyrolyseen Milieu Ouvert et Fermé. Oil and Gas Science and Technology 44, 387-411.

Burnham, A. K., Braun, R. L., Gregg, H. R., Samoun, A. M., 1987. Comparison of Methods for Measuring Kerogen Pyrolysis Rates and Fitting Kinetic Parameters. Energy and Fuels 1, 452.

Burnham, A. K., Braun, R. L., Samoun, A. M., 1988. Further Comparison of Methods for Measuring Kerogen Pyrolysis Rates and Fitting Kinetic Parameters. Organic Geochemistry 13 (4-6), 839-845.

Lewan, M. D., 1997, Experiments on the Role of Water in Petroleum Formation. Geochimica et Cosmochimica Acta, 61, 3691-3723.

Lewan, M. D. and Ruble, T. E., 2002, Comparison of Petroleum Generation Kinetics by Isothermal Hydrous and Non-Isothermal Open-System Pyrolysis. Organic Geochemistry, 33, 1457-1475.

Vandenbroucke, M., Behar, F. and Rudkiewicz, J. L., 1999, Kinetic Modelling of Petroleum Formation and Cracking: Implications from the High Pressure/High Temperature Elgin Field (u.k., northsea). Organic Geochemistry, 30, 9, 1105-1125.

Espitalie, J., Laporte, J. L., Madec, M., Marquis, F., Leplat, P., Paulet, J. and Boutefeu, A., 1977, Rapid Method for Source Rock Characterization, and for Determination of their Petroleum Potential and Degree of Evolution: Revue de l'Institut Francais du Petrole et Annales des Combustibles Liquides, 32/1, 23-42.

Espitalie, J., Makadi, K. S. and Trichet, J., 1984, Role of the Mineral Matrix During Kerogen Pyrolysis. Org. Geochem. 6, 365-382.

Basin simulators are known (see for example WO 2014/040622 A1) that notably enable determination of the production of hydrocarbons of thermogenic origin, which are hydrocarbons obtained by chemical transformation of the organic material by the effect of the high temperatures that are found in the deep subsoil.

As a general rule, the advance of a chemical reaction such as the transformation of kerogen is determined by a reaction rate law of the form:

$$\frac{dx}{dt} = -kx^n \quad (1)$$

where x represents the quantity of the chemical species concerned, n the order of the reaction, k the reaction rate constant and t time.

The reaction rate law constant k is classically determined by an empirical law. There is notably known the Arrhenius law, expressed in the form $$k = A \cdot \exp(-E/RT) \quad (2)$$

in which A is the frequency factor or pre-exponential factor, E the activation energy, R the perfect gas constant and T temperature. The parameters A and E are classically termed "kinetic parameters" of the reaction rate law.

It is important for reliable simulation of the evolution of the transformation of the organic material and therefore the quantity of hydrocarbons produced over time to have a realistic estimate of the kinetic parameters (such as for example the kinetic parameters A and E of the Arrhenius law) of the reaction rate equation described above.

The kinetic parameters of a reaction rate law are classically determined by laboratory experiments relating to artificial maturing of the immature mother rock. Carrying out these experiments necessitates taking samples of the mother rock in a location of the basin under study where the latter has not yet commenced its process of thermal transformation. The laboratory experiments may be sequences of heating samples of organic material in an inert atmosphere, such as described in the patents EP 0691540 B1 corresponding to U.S. Pat. No. 5,843,787) and FR 3021749 corresponding to US published application 2015/0346179, or by heating the organic material in gold tubes (cf. for example (Ungerer 1990)). The experiment times shorter than in the natural environment are compensated by the use of higher temperatures (between 300 and 700° C. in the laboratory as against 80 to 200° C. in the natural environment). On the basis of the measurements carried out during these experiments, it is possible to estimate the kinetic parameters associated with the reaction rate equation described above. Once this determination has been done, the reaction rate law as described above may be used in a basin model that simulates the evolution of temperature over geological time periods and thus estimates the advance of the transformation of the mother rock (and therefore the volumes of petroleum generated) throughout the latter. It is nevertheless known (cf. in particular the document (Burrus, 1997)) that there is no unique solution for the kinetic parameters (such as the parameters A and E) enabling reproduction of the measurements carried out in the laboratory. In other words values of the kinetic parameters may be satisfactory for the laboratory measurements but lead to aberrant maturing predictions after extrapolation to the real geological conditions.

Moreover, the experiments described above are costly in terms of data acquisition time. In fact, each mother rock has its own kinetic and it would therefore be necessary to repeat the data acquisition process for each of the mother rocks under study. Also, carrying out these experiments necessitates samples of immature mother rock, which in practice is not always possible. Thus it is classic to have recourse to analogs of the mother rock under study for which measurements have already been carried out or even for which kinetic parameters have previously been determined (as for example in the document (Pepper and Corvi, 1995)). Nevertheless, it is possible for the reactivity of the mother rock analog not to represent perfectly the reactivity of the mother rock really present in the basin under study. It can then happen that the results of the basin simulation integrating a reaction rate law established on the basis of geological analogs are not consistent with the reaction advance markers actually measured in the sedimentary basin (such as the rate of transformation of the organic material or the Tmax that corresponds to the temperature of the hydrocarbon compound release peak). Now this inconsistency leads to a poor estimate of the volumes of hydrocarbons generated by the mother rock by the basin simulation. It is then necessary to render consistent both the kinetic and the thermal history of the basin.

At present there is no method enabling such consistency to be obtained and so the user of the basin simulation, if noting an inconsistency, has to test by trial-and-error various hypotheses concerning the values of the kinetic parameters until a more satisfactory consistency is obtained. This leads to longer calculation times (a basin simulation is required for each trial) and a subjective result (the user defines in a more or less arbitrary manner the values of the parameters to be tested and what is more the combinations of values of the kinetic parameters to be tested).

SUMMARY OF THE INVENTION

The present invention alleviates these disadvantages. In fact, the present invention enables automatic updating without arbitration by the user of the kinetic parameters of the reaction rate law defined above either by laboratory measurements or by reference to a geological analog the reaction rate law of which has already had its parameters determined, to render consistency with the thermal history of the basin and with the measurements relating to the evolution of the maturity of the mother rock over geological time periods. Thus the present invention enables improvement of the predictions of the basin simulation and the scale of the basin.

Generally speaking, the present invention updates the kinetic parameters of a reaction rate law conjointly that reproduce measurements made on a laboratory scale (simulated or measured directly) and measurements made at the scale of the basin, combined with the thermal history obtained from the (calibrated or non-calibrated) basin simulation. Thus the method according to the invention enables determination of the kinetic parameters taking account of all the information available on the basin under study, thus contributing to a better prediction of the petroleum potential of the basin under study.

The present invention is a method executed by a computer for determining at least one of the quantity and the quality of the hydrocarbons present in a sedimentary basin, in which the hydrocarbons have been generated by maturing of the organic material of a mother rock of the basin, the sedimentary basin having undergone geological events defining a sequence of states of the basin, by use of a numerical basin simulation executed on computer, based on values representing the artificial maturing of an immature sample representing the mother rock and a sequence of artificial maturing temperatures. The method comprises at least the following steps:

A. physical parameters relating to the basin are measured by sensors, the measurements comprising at least measurements of petrophysical properties of the basin, measurements representing the thermicity of the basin for the measurements of the states of the advance of the maturing of the organic material of the basin;

B. by using the numerical basin simulation, a basin model is determined for each of the states as a function at least of the measurements of the petrophysical properties and at least one historical record of the temperatures of the basin for the states is determined;

C. values of kinetic parameters of a reaction rate law representing the evolution of the maturing of the organic material for each of the states are determined, minimizing simultaneously:
  a difference between values predicted by the reaction rate law applied with the historical record of temperatures of the basin determined for the states, and the measurements of the advance of the maturing of the organic material, and
  a difference between values predicted by the reaction rate law applied according to the sequence of temperatures for the artificial maturing and the values representing the artificial maturing;

D. at least one of the quantity and the quality of the hydrocarbons is determined from the kinetic parameters of the updated reaction rate law and the historical record of temperatures for the states.

At the end of step B, a historical record of the temperatures of the basin may advantageously be determined and calibrated by updating the historical record of the temperatures of the basin as a function of the measurements of the thermicity of the basin for the states and the step C may be applied by use of the calibrated historical record of the temperatures.

According to one embodiment of the invention, the immature sample representing the organic material may be directly sampled in the basin.

Alternatively, the immature sample representing the organic material may be sampled in a geological analog of the basin.

According to one embodiment of the invention, the values representing the artificial maturing of the immature sample may correspond to measurements of artificial maturation made on the immature sample.

The measurements of artificial maturation may advantageously be made by placing the immature sample in an inert atmosphere and subjecting it to the sequence of temperatures for the artificial maturing and then measuring a quantity of hydrocarbons released during the sequence of temperatures for the artificial maturation.

Alternatively, the values representing the artificial maturation may be obtained from the reaction rate law applied to a first estimate of the kinetic parameters.

According to one embodiment of the invention, the minimization is effected by a gradient method.

According to one variant of the invention, there may be defined based on the at least one of quantity and quality of the hydrocarbons from the basin a scheme for operation of the basin and the exploitation of the basin as a function of at least one of the quantification and the scheme.

Moreover, the invention concerns a computer program product which may be downloadable from at least one of a communication network and stored on a tangible computer readable medium for execution by a processor, program code instructions for the execution of the method as described above when the program is executed on a computer.

Other features and advantages of the method according to the invention will become apparent on reading the following examples of nonlimiting embodiments with reference to the appended figures described hereinafter.

DETAILED DESCRIPTION OF THE INVENTION

Figure 1:
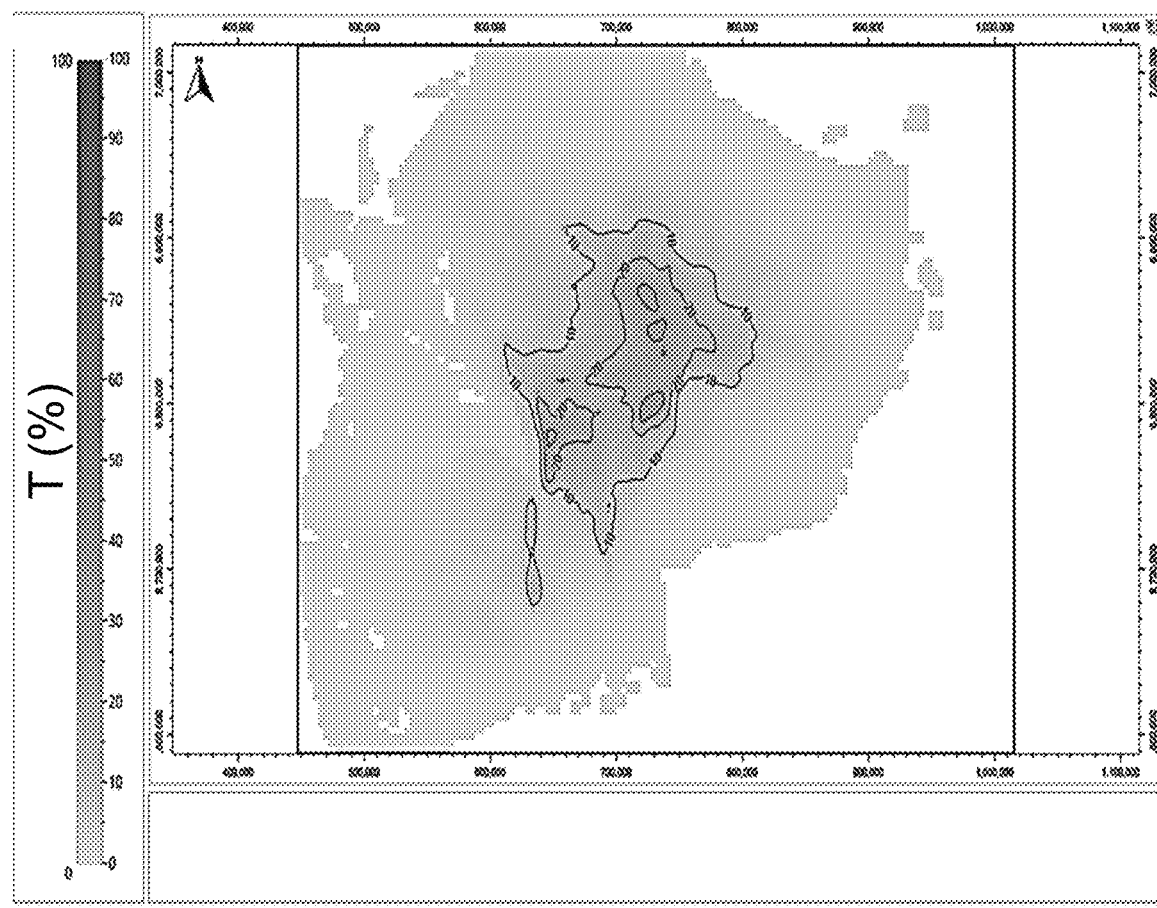
FIG. 1 is a map representing the transformation rate T (%) obtained by use of a prior art method applied to the Paris basin.

Generally the invention concerns a method for determining at least one of the quantity and the quality of the hydrocarbons present in a sedimentary basin in which the hydrocarbons have been generated by maturing of the organic material of a mother rock of the basin and in which the sedimentary basin has undergone geological events defining a sequence of states of the basin.

The method according to the invention is implemented by use of a numerical basin simulation executed on computer. A basin simulator classically enables reconstitution of at least one of the geological and the geochemical processes that have affected the basin from a geological time t to the present day. The period over which the history of this basin is reconstituted is classically discretized in terms of geological events, termed states hereinafter and denoted $\{A_i\}_{i \in [0,n]}$. Thus two states are separated by a geological event (corresponding for example to a particular sedimentary deposit and possibly extending between about one hundred years and a few million years). A basin simulator relies on a meshed representation of the basin, also referred to as a "basin model". The basin simulator enables determination of a model for each state. Thus, a basin simulator enables calculation of the physical parameters relating to the basin under study in each mesh of the meshed representation associated with each state. The physical parameters estimated by a basin simulator include temperature, pressure, porosity and mass per unit volume of the rock contained in the mesh concerned, the water velocities, and the TOC (organic material content of the rock). The basin simulator used classically also enables calculation of the quantity of hydrocarbons of thermogenic origin. The water velocities may be calculated as described in the document (Marsily, 1986), and the other physical quantities cited above may be calculated as described in the document (Schneider et al., 2000). Thus the simulation of the basin solves a system of differential equations defining the evolution over time of the physical parameters under study. To this end there may for example be used discretization by the finite volumes method as described for example in (Scheichl et al., 2003). For each state $A_i$, it is necessary to solve the equations using small time increments (i.e. with a small time step dt) up to the next state $A_{i+1}$. According to the principle of finite volume methods centered on the meshes, the unknowns are discretized by a constant value per mesh and the (mass or heat) conservation equations are integrated in space over each mesh and in time between two successive time steps. The discrete equations then express the fact that the quantity conserved in a mesh at a given time step is equal to the quantity contained in the mesh in the preceding time step increased by the flows of quantities that have entered the mesh and reduced by the flows of quantities that have left the mesh via its faces, plus external inputs.

The basin simulator according to the invention enables at least simulation of the evolution of the temperatures in each mesh of the meshed representation of each of the basin models. One example of a basin simulator of this kind is the TemisFlow™ software (IFP Énergies nouvelles, France).

The method according to the invention includes at least the steps described hereinafter.

1. Measurements of Physical Parameters 1.1. Measurements Relating to the Thermicity of the Basin During this step, it is a question of acquiring by use of sensors measurements relating to the thermal history of the basin. These measurements may be made in at least one well passing through the basin for which thermicity data is acquired during at least one of the drilling of the well, the exploration and the exploitation of the basin. These measurements may also be made based on samples taken for example in a well passing through the basin. This thermal data may be direct measurements of the temperature in the basin, at least one of measurements of vitrinite reflectance (which reflects the maturity of the basin) and measurements of transformation of the organic material of the sedimentary basin.

Thus the measurements of the current thermicity may be acquired during drilling and by various methods, such as for example direct measurement of the temperature all along the well, estimation of the thermal gradient using probes on seabed surface layers, or even the well bottom temperature from the "Drill Stem Test" (DST) measured in the drilling fluid after operations cease. All these measurements provide information on the current temperature field in the sedimentary basin.

It is also possible to use geochemical indicators that can provide elements relating to the paleotemperatures that the geological formations have undergone. The most widespread of these is the vitrinite reflectance. This is estimated by measuring the reflection of light in a thin plate using polarized light. The thin plates may be prepared from core samples taken in the well or from "cuttings" (rock fragments and residues that come to the surface with the sludge during drilling). In practice, the measurement of the vitrinite depends on the maximum temperature that the sample has been exposed to.

Also known are other geochemical indicators such as the Conodonts deterioration index, mineral transformations of clays, fission of apatite, biomarkers or again fluid inclusions. These markers can provide complementary information to vitrinite. Known in particular are the fluid inclusions that may provide information on the age of the temperature maximum or the fission of apatite that can date some geological events in an absolute manner.

1.2. Measurements Relating to the Maturing of the Mother Rock of the Basin

During this step it is a question of acquiring with of sensors measurements relating to the maturing of the mother rock of the basin.

These measurements are taken from rock samples taken (by core sampling or from cuttings) in wells passing through the basin under study, such as exploration wells. These experiments may be carried out on samples of different kinds (crude rock, kerogen, extract, . . . ). There are numerous experimental approaches enabling study of the advance and the nature of the reactions transforming the organic material.

The approaches routinely used include sequences of heating samples in an inert atmosphere, as carried out by use of the ROCK-EVAL™ device (IFP Energies nouvelles) and described in the EP patent 0691540 B1 corresponding to U.S. Pat. No. 5,843,787 and FR 3021749 corresponding to US published application 2015/0346179, or heating sequences in gold tubes (Ungerer 1990), experiments in an anhydrous closed environment (e.g. pyrolysis in a gold tube) or in an aqueous closed environment (Lewan, 1997; Lewan and Ruble, 2002). The quantity of hydrocarbon compounds released during this heating sequences are then measured, and are therefore a quantity dependent on at least one of time and temperature.

The heating sequences to which a sample is subjected may comprise ramps (with gradients from 0.1° C./minute to several tens of degrees per minute) and/or isothermal constant temperature periods (at 100° C., 250° C., 600° C., etc.), in which constant temperature periods may be between a few hours and a few weeks. The heating ramps approximate best the real conditions for which the increase of temperature of the geological medium as a function of time may be approximated by a constant. According to one embodiment of the invention, it is possible based on a heating sequence of this kind at least to determine the temperature for which the release of hydrocarbon compounds is the highest (hydrocarbon compound release peak temperature), classically denoted Tmax, and classically used as a maturity indicator (Espitalié et al., 1977).

According to an embodiment of the invention in which a constant temperature heating sequence is used, the advance of the transformation of the source as a function of time may be determined analytically (utilizing a formalism of the Arrhenius law type as described above for example).

1.3 Measurement of Physical Parameters Relating to the Basin Simulation

These measurements are required for the execution of a numerical basin simulation, in particular to fill the meshes of the meshed representation reproducing the sedimentary basin under study as described in step 2 hereinafter. These measurements may be outcrop studies, seismic acquisition campaigns, measurements in wells (by diagraphy for example), petrophysical/geochemical analyses of core samples taken in situ. On the basis of these measurements, it is possible to deduce therefrom petrophysical properties associated with the basin under study, such as facies, porosity, permeability, saturation or again the organic material content at measuring points of the basin.

2. Basin Simulation

A basin model is determined for each state $\{A_i\}$ of the basin as a function of the measurements of the physical parameters described in step 1.3 by use of a numerical basin simulation.

According to the invention, a prior art simulator is used for this. A basin simulation classically includes three steps:

A geomodelling step which constructs a meshed representation of the basin under study at the present time. This meshed representation is most often structured in layers, that is a group of meshes is assigned to each geological layer of the modelled basin. Each mesh of this meshed representation is then filled with one or more petrophysical properties such as porosity, facies (clay, sand, etc.) or the organic material content. The construction of this model is based on measurements of physical parameters as described above (cf. step 1.3). It is a question of constructing during this step a meshed representation of the basin under study at the present time. This model of the basin is generally represented on a computer, in the form of a mesh or grid, each mesh being characterized by one or more properties relating to the basin (such as facies, porosity, permeability, saturation or the organic material content at the time of sedimentation).

A step of structural reconstruction of the architecture of the basin which is a reconstruction of the past architectures of the basin for the various states. To this end, the meshed representation constructed in the preceding step that represents the basin at current time is deformed in order to represent the anti-chronological evolution of the architecture of the subsoil during geological time periods for the various states $A_i$. Thus a meshed representation is obtained for each state $A_i$.

According to one embodiment of the present invention, the structural reconstruction may be particularly simple if it is based on the hypothesis that its deformation is the result only of a combination of vertical movements by compacting of the sediment or by upheaval or deflection of its base. This technique, known as "backstripping" (or "décompaction progressive du basin" in French) is described for example in (Steckler and Watts, 1978).

According to another embodiment of the present invention, in the case of basins that have a complex tectonic history, notably in the case of basins including faults, it is necessary to use techniques with less restrictive hypotheses, such as structural restoration. Structural restoration of this kind is described for example in the document FR 2 930 350 A corresponding to US published patent application 2009/0265152 A. Structural restoration calculates the successive deformations that the basin has undergone, integrating the formation caused by compaction and resulting from tectonic forces.

A basin simulation step is performed which is a numerical simulation of a selection of physical and chemical phenomena occurring during the evaluation of the basin and contributing to the formation of the petroleum traps, as described above. This basin simulation is carried out for each state and relies for each state $A_i$ on the meshed representation constructed for the state $A_i$ concerned as described in the preceding step. The basin simulator therefore determines a basin model for each state in which each of the meshes of that model comprises physical parameters, including at least the temperature for the use of the method according to the invention, and, advantageously, the pressure, the porosity, the mass per unit volume of the rock, the water velocities, and the TOC (or organic material concentration of the rock), etc. One example of a simulator of this kind is the TemisFlow™ software (IFP Energies nouvelles, France).

Following basin simulation of this kind, a basin model is obtained for each of the states Ai in which each mesh of each of these models being filled with at least one value of the temperature predicted by the numerical basin simulation.

A historical record of the thermicity of the basin can then be extracted for at least the states Ai. It is for example possible to extract a historical record of the temperatures in particular meshes of the basin models simulated in this way (as a general rule at the base of the sedimentary basin) representing the evolution of the temperatures in those meshes over time and at least for the simulated states Ai.

3. Thermal Calibration of the Basin Models

This step is optional. During this step the basin models are thermally calibrated by adjusting the thermal historical record obtained from the basin models as a function of the measurements representing the thermicity of the basin described in step 1.1 above (for example direct temperature measurements or measurements of vitrinite reflectance, measured in drilling wells or on outcrops).

According to one embodiment of the invention, a historical record of the thermicity of the basin under study is determined on the basis of basin models filled in with temperatures and determined for each state following the preceding step. This historical record is compared to the measurements relating to the thermal history of the basin previously made in situ. The historical record of thermicity obtained from the basin simulation is then updated on the basis of the historical record determined by the thermicity measurements, imposing the temperature values measured at the measurement points, and interpolating those values in three dimensions, taking account of the thermal model obtained from the basin simulation. FR 2 996 038 describes one such thermal calibration method.

Following this step, a calibrated historical record of the temperatures of the basin under study is obtained. This historical record comprises at least one calibrated temperature value for each of the states Ai.

4. Determination of the Kinetic Parameters of a Reaction Rate Law for the Maturing of the Mother Rock According to the invention, and in the classic manner, the reaction rate law representing the evolution of the maturing of the organic material of the basin under study is given by a formula of the type:

$$\frac{dx}{dt} = -kx^n \quad (1)$$

where x represents the quantity of the chemical species concerned, n is the order of the action, k is the reaction rate law constant and t is time.

According to one embodiment of the invention, the Arrhenius law is used to represent the reaction rate law constant, that is to say:

$$k = A \cdot \exp(-E/RT) \quad (2)$$

where A is the frequency factor or pre-exponential factor, E is the activation energy, R is the perfect gas constant and T is the temperature. The parameters A and E of the Arrhenius law are classically termed kinetic parameters of the reaction rate law.

According to another embodiment of the invention the reaction rate law constant is represented by a law of the type (Stainforth, 2009):

$$k = \left(\frac{k_B T}{h}\right) \cdot \exp\left(-\frac{\Delta G}{RT}\right) \quad (3)$$

in which, in contrast to the Arrhenius law, the pre-exponential factor $$\left(A = \left(\frac{k_B T}{h}\right)\right)$$

is variable and depends on T, E is another physical definition, and $k_B$ is the Boltzmann constant, h is the Planck constant and $\Delta G$ is the molar free enthalpy.

According to the invention the kinetic parameters of this reaction rate law are determined by minimizing simultaneously:

i. the difference between the values predicted by the reaction rate law with the law being applied with the historical record of temperatures of the basin determined in step 2 (non-calibrated temperature historical record) or step 3 (calibrated temperature historical record), and the measurements of the advance of the maturing of the organic material made in situ (cf. step 1.2 above); and ii. the difference between the values predicted by the chosen reaction rate law is applied in accordance with a sequence of temperatures for the artificial maturing and the values representing the artificial maturing of an immature sample representing of the mother rock of the basin under study obtained for the same sequence of artificial maturing temperatures.

The provenance of the values representing the artificial maturing of an immature sample representing the mother rock of the basin under study are described in detail hereinafter.

According to a first variant embodiment of the invention, the values representing the artificial maturing of an immature sample representing the mother rock of the basin under study result from laboratory experiments is carried out on an immature sample of the mother rock of the basin taken directly in the basin under study. The laboratory experiments may be sequences of heating samples of organic material in an inert atmosphere, such as described in EP 0691540 B1 corresponding to U.S. Pat. No. 5,843,787 and FR 3021749 corresponding to US published patent application 2015/0346179, or a sequence of heating the organic material in gold tubes (Ungerer 1990).

Nevertheless, an immature sample of this kind of the organic material taken directly in the basin under study is very often not available. According to a second variant embodiment of the invention if a sample obtained from a geological analog for the basin under study is available, the values representing the artificial maturation of an immature sample representing the mother rock of the basin under study result from laboratory experiments carried out on a sample taken in a geological analog of the basin under study. The laboratory experiments may heat samples of organic material in an inert atmosphere in sequences, such as described in EP 0691540 B1 corresponding to U.S. Pat. No. 5,843,787 and FR 3021749 corresponding to US published patent application 2015/0346179, or a sequence of heating the organic material in gold tubes (Ungerer 1990).

According to a third variant embodiment of the invention, if no immature sample representing the mother rock of the basin is available, there may be used measurements of artificial maturation of an immature sample representing the mother rock of the basin under study referenced in the literature, carried out on an immature sample obtained from the basin under study or an immature sample obtained from a geological analogue of the basin under study.

According to a fourth variant embodiment of the invention in which there are not available any measurements of artificial maturation made on an immature sample representing the mother rock of the basin under study (obtained from the basin under study or from a geological analog) but there are available kinetic parameter values representing the mother rock of the basin under study, there may be synthetically created values representing the artificial maturation of the mother rock under study by applying a reaction rate law with parameters set with the available kinetic parameter values and a sequence of temperatures representing the artificial maturation. These kinetic parameter values may have been predetermined on implementation of the present invention or come from referencing studies in the field. An example of a study of this kind referencing kinetic parameter A and E values of the Arrhenius law can be found in the document (Pepper and Corvi, 1995). According to this variant embodiment of the invention, there are simulated on the basis of the values of the kinetic parameters obtained from the literature and applicable to the basin under study values reproducing artificial maturing of the mother rock that would be carried out in the laboratory with a sequence of temperatures characteristic of the artificial maturing laboratory measurements. There may be simulated for example, by use of a reaction rate law, a laboratory experiment that would employ a sequence of temperatures comprising heating of the sample for 15 minutes at 300° C. followed by an increase of 25° C. per minute up to 700° C. Other heating historical records may equally be used, such as for example a constant temperature during different time intervals as may be employed for gold tube experiments.

Thus this step updates the kinetic parameters of the reaction rate law (such as for example the parameters A and E of the Arrhenius law) to reproduce both measurements made on a laboratory scale (either simulated or directly measured) and measurements made on the scale of the basin, combined with the (calibrated or non-calibrated) thermal historical record obtained from the basin simulation.

Minimization in accordance with the invention is classically carried out in two steps: initial values are determined for the kinetic parameters (cf. step 4.1 below) after which the kinetic parameters are updated (cf. step 4.2 below).

4.1. Estimation of the Initial Values of the Kinetic Parameters

During this substep, determining initial values for the kinetic parameters of the reaction rate law is performed. These values are determined as a function of the available artificial maturation measurements (see above).

According to the first, second and third variant embodiments of the invention described above, for which there are available artificial maturation measurements made on an immature sample representing the mother rock of the basin under study (directly sampled or taken from an analog), initial values of the kinetic parameters of the chosen reaction rate law are estimated by inversion of the artificial maturation measurements. According to an implementation of the invention in which the chosen reaction rate law is the Arrhenius law, the parameters A and E of that law are determined based on these artificial maturation measurements. According to one implementation of the invention, the procedure of inversion of the laboratory artificial maturing measurements comprises two phases:

In a first phase, the parameter A is fixed and the distribution of the parameter E is optimized by a least squares method.

In a second phase, different values of the parameter A are tested in order to obtain an optimum calibration between a theoretical curve and the maturing measurements.

According to the fourth variant embodiment of the invention described above, for which artificial maturation measurement values are simulated synthetically based on predetermined kinetic parameter values, the values of those parameters are used directly to initialize the chosen reaction rate law. An example of a study of this kind referencing values of the kinetic parameters A and E of the Arrhenius law can be found in the document (Pepper and Corvi, 1995).

There is obtained after this step, a reaction rate law set with initial kinetic parameter values. Those parameter values are to be optimized in the step 4.2 described below.

4.2. Updating the Kinetic Parameter Values

The values of the kinetic parameters of the reaction rate law are updated during this step.

According to the first, second and third variant embodiments of the invention for which there are available measurements reproducing the maturation of an immature sample taken directly in the basin under study or obtained from a geological analog of the basin, updating in accordance with the invention is carried out so as to minimize simultaneously:

the difference between the values predicted by the reaction rate law with the law being applied with the historical record of temperatures of the basin determined in step 2 (non-calibrated temperature historical record) or step 3 (calibrated temperature historical record) and the measurements in advance of the maturation of the organic material carried out in situ (cf. step 1.2 above), and a difference between the values predicted by the reaction rate law with the law being applied with the sequence of temperatures used for the artificial maturation experiments, and the values of the measurements reproducing the artificial maturation.

According to the fourth variant embodiment of the invention for which there are not available direct measurements of the maturation of an immature sample but maturation measurements as simulated numerically, the updating of the kinetic parameters is applied in the following manner, minimizing simultaneously:

the difference between the values predicted by the reaction rate law with the law being applied with the historical record of temperatures of the basin determined in step 2 (non-calibrated temperature historical record) or step 3 (calibrated temperature historical record) and the measurements of advance of the maturing of the organic material made in situ (cf. step 1.2 above), and the difference between the values predicted by the reaction rate law with the law being applied with the sequence of temperatures used to simulate an artificial maturation experiment, and the values of that simulated artificial maturation. Accordingly, in accordance with this fourth variant embodiment of the invention, the simulated values of artificial maturation serve as constraints for stabilizing the inversion of the advance measurements.

Accordingly, the kinetic parameters of the reaction rate law (such as for example the parameters A and E of the Arrhenius law) are updated to reproduce both measurements on a laboratory scale (simulated or directly measured) and measurements made on the scale of the basin, combined with the thermal historical record obtained from the basin simulation (calibrated or non-calibrated).

Any method may be used to update the kinetic parameters (basin reaction, by gradient, by linear regression, . . . ).

According to one implementation of the invention, a gradient method is used as implemented for example in the CougarFlow™ software (IFP Energies nouvelles, France). It uses a method of greater slope to determine the minimum of an objective function. This type of method generally gives access to a single optimum of the cost function that may be a local minimum. It is therefore aimed only at a model adjustment objective.

According to another implementation of the method, a basin approach is used. This method estimates an a posteriori probability distribution of the parameterization of a model. This distribution therefore provides access to an optimum model but also to information enabling estimation of uncertainties in the parameterization of the model and taking account of the latter in the predictions produced. Moreover, this method enables access to an overall optimum but may on the other hand necessitate the execution of a greater number of simulations. The probability distributions may thereafter be used to determine an optimum parameterization and to propagate all the parameterization uncertainties of the model onto the values of the properties to be predicted.

5. Determination of the Quantity and/or the Quality of the Hydrocarbons

At least one of the quantity and the quality of the hydrocarbons present in the sedimentary basin under study are determined during this step on the basis of the updated kinetic parameters of the reaction rate law and the temperature historical record resulting from step 2 (calibrated temperature historical record) or step 3 (non-calibrated temperature historical record).

According to the invention the updated reaction rate law is applied in each of the meshes of each of the basin models comprising organic material to calculate the level of transformation of that organic material over time (for each state Ai) while taking account of the temperature historical record obtained from step 2 (non-calibrated temperature historical record) or preferably step 3 (calibrated temperature historical record).

At least one of the quantity and the quality of the hydrocarbons present in the basin at the present time are determined in this way in a more reliable way than using a prior art basin simulator because the reaction rate law is parametered to account for all of the available kinetic information, including measurements on a laboratory scale (simulated or directly measured) and measurements made on the scale of the basin. Also, according to one implementation of the invention, account may be taken of a calibrated thermal model (one as described in step 3 is possible), which further improves the reliability of the results obtained in terms of the quantity and the quality of the hydrocarbons present in the basin.

According to one implementation of the invention, there is also used information concerning the thickness of the mother rock, its richness in organic material, the fluids generated in order for the prediction of at least one of the quantity and the quality of the hydrocarbons present in the basin to be as reliable as possible.

Accordingly, the method according to the invention enables the having to employ a trial-and-error technique to test different hypotheses until consistency is obtained with the measurements carried out in situ, whilst continuing to conform to the laboratory measurements. This results in shorter calculation times (there is no longer a basin simulation to be launched for each trial), as well as a more objective result (the user no longer defines in a more or less arbitrary manner the values of the parameters to be tested and, moreover, the combinations of parameter values to be tested).

Accordingly, the present invention enables automatic updating, without arbitration by the user of the kinetic parameters of the reaction rate law defined above to provide consistently with the thermal historical record of the basin and with the measurements relating to the evolution of the maturing of the mother rock in geological times. The present invention therefore enables improvement of the predictions of the basin simulation on the scale of the basin.

6. Exploitation of the Hydrocarbons of the Formation

At the end of the foregoing steps, there is available at least one of the quantity and the quality of the hydrocarbons present in each of the meshes of the meshed representation at the present time.

Moreover, depending on the basin simulator being used to implement the invention, there may be available information on, for example:

i. the placement of the sedimentary layers,
ii. their compaction because of the effect of the weight of overlying sediments,
iii. their heating during their burial,
iv. the modifications of fluid pressures resulting from this burial,
v. the formation of the hydrocarbons formed by thermogenesis,
vi. the movement of these hydrocarbons in the basin because of the effect of buoyancy, capillarity, pressure gradient differences in the underground flows.

Based on such information, knowledge is available of the zones of the basin corresponding to meshes of the meshed representation of the basin at the present time including hydrocarbons together with the content, nature and pressure of the hydrocarbons that are trapped therein. Therefore selection of the zones of the basin under study having the best petroleum potential is possible.

Petroleum exploitation of the basin may then take a number of forms, in particular:

carrying out exploratory drilling in the various zones selected as having the best potential in order to confirm or to rule out the potential that was estimated beforehand and to acquire new data for employing new and more precise studies; and exploitation drilling (producer or injector wells) for the recovery of the hydrocarbons present in the sedimentary basin in the zones selected as having the best potential.

Equipment and Computer Program Product

The method according to the invention is executed by equipment (for example a computer workstation) comprising data processing (a processor) and data storage (a memory, in particular a hard disk), together with an input and output interface for entering data and outputting the results of the method.

The data processing means are configured to execute the following steps:

using a numerical basin simulation, a basin model is determined for each of the states Ai as a function at least of the measurement of the petrophysical properties and at least one historical record of the temperatures of the basin is determined for the states;

determining values of the kinetic parameters of the reaction rate law representing the evolution of the maturing of the organic material for each of the states, minimizing simultaneously:

a difference between the values predicted by the reaction rate law applied with the historical record of temperatures of the basin determined for the states and the measurements of the advance of the maturation of the organic material; and a difference between the values predicted by the reaction rate law applied in accordance with the sequence of temperatures for the artificial maturation and the values representing the artificial maturation;

at least one of the quantity and the quality of the hydrocarbons is determined based on the kinetic parameters of the updated reaction rate law and the historical record of temperatures for the states Ai.

Moreover, the invention concerns a computer program product, which is downloadable from at least one of a communication network and stored on a computer readable tangible medium which is executable by a processor, comprising program code instructions for the execution of the method as described above when the program is executed by a computer.

Example of Implementation

The features and advantages of the method according to the invention will be more clearly apparent on reading the following application example.

The method according to the invention is applied to the basin of Paris (France). This basin is a sedimentary downfold of 140 000 km$^2$, 500 km from East to West by 300 km from North to South, formed of concentric sedimentary layers typical of intracratonic basins. Up until now, more than 240 million barrels have been recovered in the 52 exploitation fields.

The exploration and the exploitation of this basin have led to taking numerous samples in situ, notably analyzed by use of the ROCK-EVAL® device (IFP Energies nouvelles, France), as described in EP patent 2342557 corresponding to U.S. Pat. No. 8,796,035.

For the purposes of the use of the method according to the invention, the numerical model representing the Paris basin covers all of the sedimentary basin and all of the deposits from the surface to the base. The horizontal definition, that is the size of a single cell, is 2 km×2 km. Chronologically, the numerical model reproduces a succession of 38 geological events, comprising 31 deposits of sedimentary formations and 7 erosion events.

According to one implementation of the invention, the thermal historical record of the model is calibrated over a large volume of data, namely tens of wells containing measured temperature and vitrinite information. To this classic information are added less routine constraints in the form of fluid inclusions and "clumped isotopes", which are paleo-thermo-chronometers, that is these measurements provide information on the temperature observed in the formation at a certain age.

The principal mother rocks from which the hydrocarbons in place originate are Toarcian and Hettangian. The method according to the invention has been applied to the Hettangian mother rock but could very well have been used for the second mother rock. The mother rock studied is a marine mother rock of type II having a moderate organic carbon content (from 0.7% to 1.2%).

The method according to the invention is applied in accordance with the fourth variant embodiment of the invention for which the values representing the artificial maturing are simulated numerically on the basis of predetermined kinetic parameter values. In fact the Paris basin being well known, it is possible to use kinetic parameter values known in the literature to create values simulating artificial maturation measurements.

The reaction rate law chosen is the Arrhenius law (cf. equation 2). The available advance measurements correspond to eleven measurement values of the Tmax of the Hettangian mother rock, spatially well distributed over the whole of the basin, at the level of the prospective zones.

Figure 3:
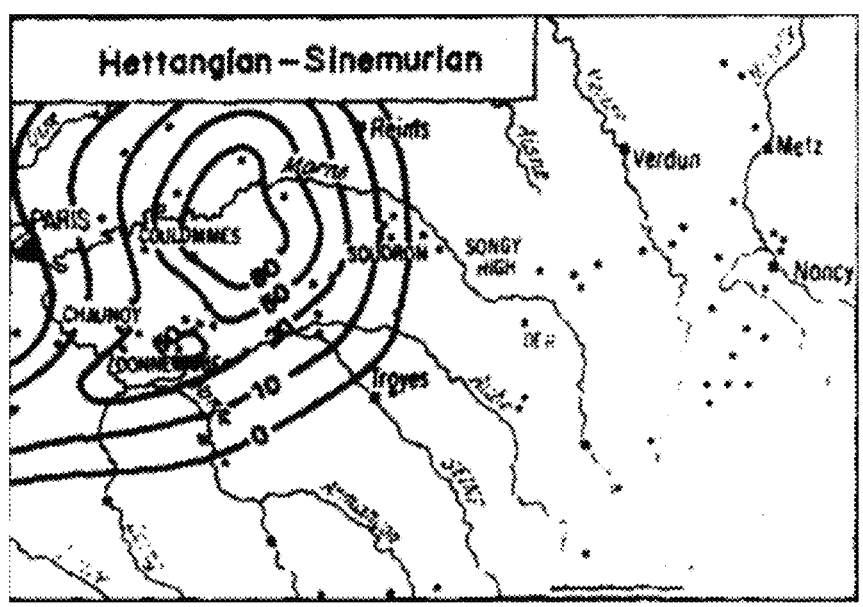
FIG. 3 is a map representing the transformation rate T (%) obtained by extrapolation of values measured at wells drilled in the Paris basin extracted from (Espitalié, 1987).

Table 1 compares the values of Tmax measured in the mother rock samples and the values of Tmax determined by a prior art method. There may be seen some difference between the prior art predictions of Tmax and the measured Tmax. FIG. 1 shows a map of transformation rates obtained at the present time for the Hettangian mother rock by application of a prior art method. It can be seen that the prior art method does not predict transformation level values of around 20% maximum in the center of the basin. These values do not agree with the measurements effected in wells drilled in the Paris basin. In fact, the map shown in FIG. 3 (extracted from (Espitalie, 1987)), which was established by extrapolation of well measurements, shows instead a maximum around 80%.

TABLE 1

|  | Measured | Simulated |
|---|---|---|
| Achere | 427 | 416.75 |
| Baulnes | 439 | 419.75 |
| Cerneux | 441 | 426.75 |
| Cesarville | 433 | 418 |
| Charmottes | 438 | 419.75 |
| Crouy | 434 | 418.75 |
| Malnoue | 445 | 423.5 |
| Nantouillet | 438 | 417.5 |
| Ouzouer | 434 | 417.25 |
| Roches | 437 | 418.5 |
| Tousson | 436 | 418 |

Figure 2:
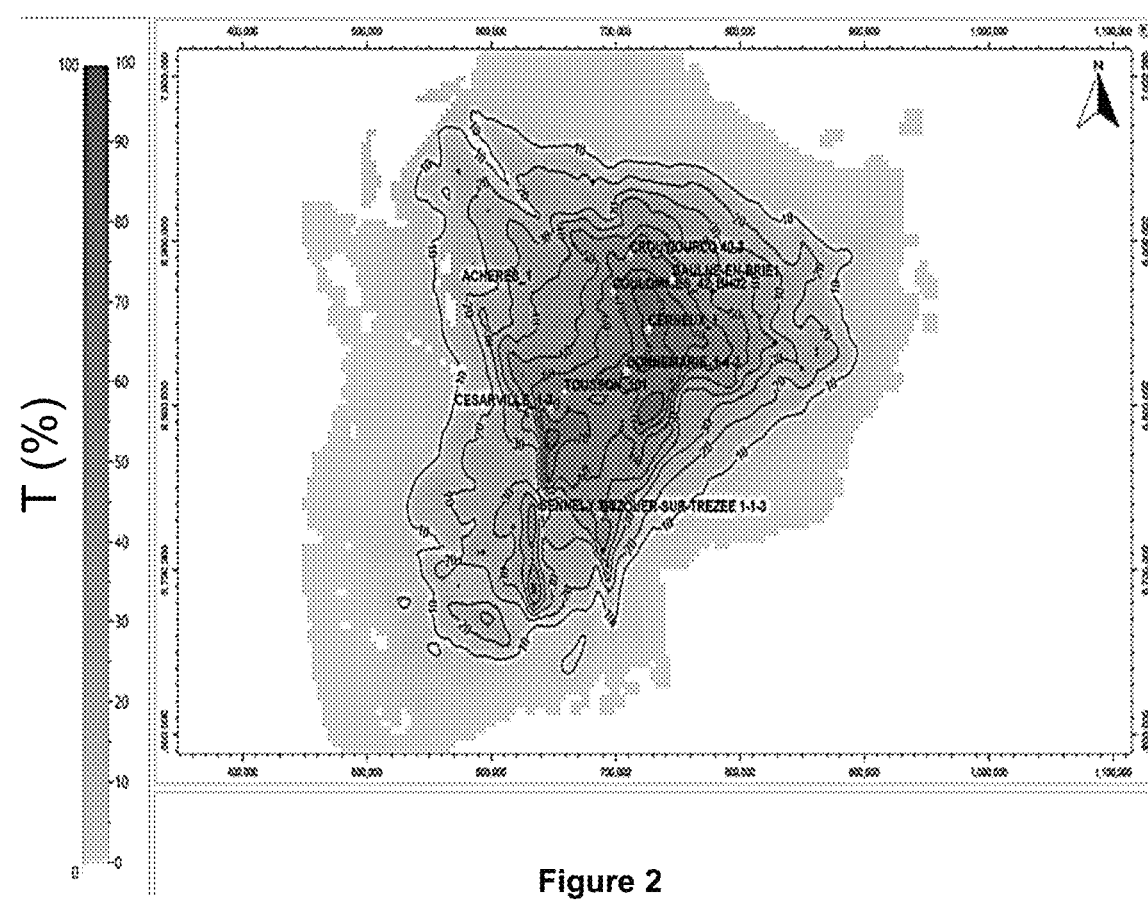
FIG. 2 is a map representing the transformation rate T (%) obtained by use of the method according to the invention applied to the Paris basin.

Table 2 compares the value of Tmax measured in the mother rock samples and the values of Tmax determined by the method according to the invention, obtained by minimizing simultaneously the measurements on the scale of the basin and the artificial maturation values (simulated on a laboratory scale). There can be seen improved calibration compared to the prior art. FIG. 2 shows the map of transformation levels obtained by application of the method according to the invention. The orders of magnitude are comparable to those estimated by (Espitalie, 1987; cf. FIG. 3). Moreover, by integration of all the physico-chemical phenomena generated by the geology, the present invention offers a more refined spatialization and also information on the whole of the basin.

TABLE 2

|  | Measured | Simulated |
|---|---|---|
| Achere | 427 | 428.75 |
| Baulnes | 439 | 437.5 |
| Cerneux | 441 | 442.25 |
| Cesarville | 433 | 437 |
| Charmottes | 438 | 437.5 |
| Crouy | 434 | 437.25 |
| Malnoue | 445 | 439 |
| Nantouillet | 438 | 436 |
| Ouzouer | 434 | 434.25 |
| Roches | 437 | 437.25 |
| Tousson | 436 | 437 |

The present invention enables automatic updating without arbitration on the part of the user of the kinetic parameters of a reaction rate law in order to ensure consistency with all of the measurements that are made. The present invention makes possible accounting for, as well as the advance measurements relating to the thermal historical record of the basin, values representing the artificial maturing of the mother rock under study (carried out on a sample taken in the basin under study or from a geological analog). The present invention improves of the predictions of the basin simulation on the scale of the basin.

The invention claimed is:

1. A method executed by a computer for determining at least one of the quantity and the quality of hydrocarbons present in a sedimentary basin, generated by maturation of organic material of a mother rock of the basin, the sedimentary basin having undergone geological events defining a sequence of states of the basin, by use of a numerical basin simulation executed on the computer, based on values representing artificial maturation of an immature sample representing the mother rock and a sequence of artificial maturation temperatures, comprising steps of:
   A. measuring physical parameters relating to the basin by use of sensors, the measurements comprising at least one of measurements of petrophysical properties of the basin, measurements representing thermicity of the basin for the states of the basin and measurements representing advancing maturation of the organic material of the basin;
   B. determining a basin model by use of the numerical basin simulation for each of the states of the basin as a function at least of the measurements of the petrophysical properties and determining at least one historical record of temperatures of the basin for the states of the basin;
   C. determining values of kinetic parameters of a reaction rate law representing evolution of the maturation of the organic material for each of the states which are determined, to minimize simultaneously:
      i. a difference between values predicted by the reaction rate law applied with the historical record of the temperatures of the basin determined for the states of the basin and the measurements representing advancing of the maturation of the organic material; and
      ii. a difference between values predicted by the reaction rate law applied according to a sequence of temperatures and the artificial maturation and the values representing the artificial maturation; and
   D. at least one of quantity and the quality of the hydrocarbons is determined from the kinetic parameters predicted by the reaction rate law and the historical record of temperatures for the states.

2. The method as claimed in claim 1 in which at the end of step B, a historical record of the temperatures of the basin is determined and calibrated by updating the historical record of the temperatures of the basin as a function of the measurements of the thermicity of the basin for the states and step C is applied by use of the calibrated historical record of the temperatures.

3. The method as claimed in claim 2 in which the immature sample representing the organic material has been directly sampled from the basin.

4. The method as claimed in claim 2 in which the immature sample representing the organic material has been sampled from a geological analog of the basin.

5. The method as claimed in claim 2 wherein the values representing the artificial maturation of the immature sample correspond to measurements of artificial maturation made on the immature sample.

6. The method as claimed in claim 1 in which the immature sample representing the organic material has been directly sampled from the basin.

7. The method as claimed in claim 6 wherein the values representing the artificial maturation of the immature sample correspond to measurements of artificial maturation made on the immature sample.

8. The method as claimed in claim 1 in which the immature sample representing the organic material has been sampled from a geological analog of the basin.

9. The method as claimed in claim 8 wherein the values representing the artificial maturation of the immature sample correspond to measurements of artificial maturation made on the immature sample.

10. The method as claimed in claim 1 wherein the values representing the artificial maturation of the immature sample correspond to measurements of artificial maturation made on the immature sample.

11. The method as claimed in claim 10 wherein the measurements of artificial maturation are made by placing the immature sample in an inert atmosphere and subjecting the sample to the sequence of temperatures for the artificial maturation and then measuring a quantity of hydrocarbons released during the sequence of temperatures for the artificial maturation.

12. The method as claimed in claim 1 wherein the values representing the artificial maturation are obtained from the reaction rate law applied to a first estimate of the kinetic parameters.

13. The method as claimed in claim 1 wherein the minimization is performed by use of a gradient method.

14. The method as claimed in claim 1 wherein based on at least one of the quantity and the quality of the hydrocarbons from the basin, a scheme for operation of the basin is defined and the sedimentary basin is exploited as a function of the at least one of quantity and the scheme.

15. A computer program product recorded on a tangible computer readable medium comprising program code instructions which are executed on a processor to perform the method as claimed in claim 1 when the program is executed on a computer.

* * * * *